(12) United States Patent
Hauk et al.

(10) Patent No.: US 7,868,203 B2
(45) Date of Patent: Jan. 11, 2011

(54) PRODUCTION OF SODIUM DIFORMATE

(75) Inventors: Alexander Hauk, Ludwigshafen (DE); Stefan Gropp, Speyer (DE); Anna Valeska Lohmann, Limburgerhof (DE); Robert Heinz, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 368 days.

(21) Appl. No.: 12/159,552

(22) PCT Filed: Dec. 28, 2006

(86) PCT No.: PCT/EP2006/070246

§ 371 (c)(1),
(2), (4) Date: Jun. 27, 2008

(87) PCT Pub. No.: WO2007/074164

PCT Pub. Date: Jul. 5, 2007

(65) Prior Publication Data

US 2009/0061060 A1  Mar. 5, 2009

(30) Foreign Application Priority Data

Dec. 29, 2005  (DE) ........................ 10 2005 062 931

(51) Int. Cl.
*C07C 53/00* (2006.01)
(52) U.S. Cl. ...................................... 562/609
(58) Field of Classification Search ........................ None
See application file for complete search history.

(56) References Cited

U.S. PATENT DOCUMENTS 6,137,005 A * 10/2000 Hj.o slashed.rnevik ...... 562/609

FOREIGN PATENT DOCUMENTS

| CA | 2 604 070 | 10/2006 |
| CA | 2 607 099 | 11/2006 |
| DE | 424017 | 1/1926 |
| EP | 0 824 511 | 8/2000 |
| WO | WO-96/35337 A1 | 11/1996 |
| WO | WO-96/35657 A1 | 11/1996 |
| WO | WO-2004/057977 | 7/2004 |
| WO | WO-2006/108652 | 10/2006 |
| WO | WO-2006/117187 | 11/2006 |

OTHER PUBLICATIONS

Gmelins Handbuch der anorganischen Chemie [Gmelin's Handbook of Inorganic Chemistry], 8th edition, No. 21, pp. 816-819, Verlag Chemie GmbH, Berlin 1928.
Gmelins Handbuch der anorganischen Chemie [Gmelin's Handbook of Inorganic Chemistry], 8th edition, No. 22, pp. 919-921, Verlag Chemie GmbH, Berlin 1937.

* cited by examiner

*Primary Examiner*—Paul A Zucker
(74) *Attorney, Agent, or Firm*—Connolly Bove Lodge & Hutz LLP

(57) ABSTRACT

The present invention relates to a process for producing a solid sodium diformate preparation having a formic acid content of at least 35% by weight based on the total weight of sodium diformate preparation, in which, at elevated temperature, an aqueous solution (E) is produced which comprises sodium formate and formic acid in a molar ratio of HCOOH:HCOONa of greater than 1.5:1 and which has a molar ratio of HCOOH:$H_2O$ of at least 1.1:1, the aqueous solution (E) is brought to crystallization to obtain a solid phase (F) and a mother liquor (G), and the solid phase (F) is separated off from the mother liquor (G), (i) the mother liquor (G) being fed to a distillation apparatus (DV);
(ii) the mother liquor (G) in the distillation apparatus (DV) being admixed with a sodium-comprising base (A) to obtain a mixture (B) comprising sodium formate and formic acid;
(iii) admixing the mixture (B) obtained from step (ii) with formic acid (D) to obtain the aqueous solution (E); and
(iv) excess water (C) essentially being ejected only by withdrawal from the distillation apparatus (DV);

and also to the use of a solid sodium diformate preparation obtainable by the inventive process as feed additive for animal feed, in particular for monogastric animal feed and especially for animal feed for hogs and/or poultry.

30 Claims, 3 Drawing Sheets

PRODUCTION OF SODIUM DIFORMATE

This application is a national phase of PCT/EP2006/070246, filed on Dec. 28, 2006, which claims priority to DE 10 2005 062 931.8 filed Dec. 29, 2005, the entire contents of all are hereby incorporated by reference.

The present invention relates to a process for producing a solid sodium diformate preparation having a high content of formic acid.

DESCRIPTION

Acid formates have an antimicrobial activity and are used, for example, for preserving and for acidifying plant and animal materials, for instance grasses, agricultural products or meat, for treating biowastes or as an additive for animal nutrition.

In the field of animal nutrition, as sodium compounds, use is generally made either of mixtures of sodium diformate with trisodium hydrogenformate or the latter alone, see, e.g., WO 96/35337 and WO 04/57977. WO 96/35337, furthermore, reports on the use of sodium diformate, no specific instructions on the production of this compound being given.

Generally, for the use of hydrogenformates, a content of formate anions as high as possible as one of the active constituents is desirable. From the economic aspect, it is advantageous, in particular if this increased content of formate anions is accompanied by a formic acid fraction as high as possible, since this simultaneously offers the acidifying activity. From these aspects, the use of sodium formate acidified by formic acid (hereinafter also referred to as sodium diformate) is particularly expedient, since, in this case, compared with trisodium hydrogentetraformate, and also compared with potassium formate acidified by formic acid (hereinafter also referred to as potassium diformate), in each case a higher theoretical content, both in formate ions and in formic acid, is present. Although both values are somewhat more expedient in the case of ammonium diformate, this is a very unstable compound, however.

Acid formates in solid form and their production have long been known as such, e.g. in Gmelins Handbuch der anorganischen Chemie [Gmelin's handbook of inorganic chemistry], 8th edition, Number 21, pages 816 to 819, Verlag Chemie GmbH, Berlin 1928, and also Number 22, pages 919 to 921, Verlag Chemie GmbH, Berlin 1937. The acid formates potassium diformate and sodium diformate are said in these citations to be obtainable in principle by dissolving potassium formate or sodium formate in formic acid and subsequent cooling. In addition to sodium diformate, the more stable crystal form trisodium hydrogentetraformate exists. However, reference is made to the fact that especially sodium diformate is accessible only with difficulty in crystalline dry form and, furthermore, is relatively unstable. The statements in Gmelin's handbook only permit the conclusion that the products described there were not pure sodium diformate.

German patent DE 424017 (of Jan. 14, 1926) teaches the production of sodium formates acidified by formic acid having various acid contents by introducing sodium formate into aqueous formic acid. The resultant crystals are obtained by cooling the solution to ambient temperature. Depending on the water content of the formic acid, in addition to trisodium hydrogenformate and mixtures of trisodium hydrogenformate with sodium diformate, sodium diformate is also reported to be accessible. The latter is said to be obtained by the process of DE 424017 when the formic acid used has a content of greater than 50%, e.g. 80%, as in Example 2.

The inventors' own experiments, however, found that, under the conditions specified in DE 424017, sodium diformate cannot be obtained in pure crystalline form. Rather, in this procedure a mixture with trisodium hydrogenformate is obtained, the formic acid content of which is markedly below the theoretical value expected for pure sodium diformate of 40.36% by weight, based on the total dry weight.

EP 0 824 511 B1 describes a process for producing products which comprise disalts of formic acid. In this process, certain alkali metal or ammonium formates, hydroxides, (bi) carbonates, or ammonia are mixed at 40° C. to 100° C. with formic acid which has a content of at least 50%. The mixture is then cooled and the disalts are obtained by filtration. Although the production of potassium formate acidified by formic acid and also of mixtures of sodium formate acidified by formic acid with trisodium hydrogentetraformate is explained by way of example, the production of solid pure sodium diformate, in contrast, is not taught. For instance, this is because the temperatures and concentration limits specified for the (aqueous) potassium and sodium formate solutions to be used for the process only permit the production of potassium diformate, since (aqueous) solutions of sodium formate, owing to the lower solubility limit, compared with potassium formate, cannot be produced in the specified concentrations. Therefore, although potassium diformate is obtained, the sodium diformate is present exclusively in a mixture with trisodium hydrogentetraformate.

Furthermore, EP 0 824 511 B1 describes a processing method in which the mother liquor obtained after the crystallization is completely neutralized (pH=9 to 10) and is concentrated to a formate content of 70 to 80%, and in which the resultant formate solution is recirculated to the starting solution used for the crystallization. In order to be able to employ this process explained in EP 0 824 511 B1 by way of example on the basis of production of potassium diformate for producing sodium diformate, the sodium formate solution to be concentrated would have to be handled at comparatively high temperatures. For instance, a 70% strength by weight sodium formate solution is only obtainable at a temperature of about 135° C., and an 80% strength by weight sodium formate solution only at a temperature of 180° C. Such temperatures require high expenditure in the heating of the apparatuses used, for example piping and valves. If, after the concentration, an 80% strength by weight sodium formate solution is recirculated and mixed, e.g. with 85% strength by weight formic acid solution, the resultant solution, owing to its high water concentration, can only be crystallized industrially with high expenditure. The crystallization temperature of such a solution is below 20° C., so that generally a refrigeration unit requiring expenditure on energy costs and capital costs is necessary. Furthermore, in the neutralization of all of the mother liquor according to the process described in EP 0 824 511 B1, too much sodium formate is produced so that, when the overall balance is considered, an excess fraction must be ejected. This cannot be avoided even by using a more highly concentrated formic acid solution.

WO 2006/108652 (=previous German application DE 10 2005 017 089.7) describes for the first time a process for producing solid sodium diformate having a formic acid content of at least 35% by weight in pure stable and dry form.

In addition, WO 2006/117187 (previous German application DE 10 2005 020 890.8) describes a process for producing such a solid sodium diformate in which the resultant amount of excess sodium formate is minimized. Although this process permits efficient utilization of the resultant mother liquor by essentially complete recirculation to the process, ejection of excess water by means of a cost-intensive concentration of the partially neutralized mother liquor is required.

Adequate stability of sodium formate acidified by formic acid in solid form is of particular importance not only with respect to handling and storage life, but also with respect to production. In particular, liberation occurring to a relatively great extent of the formic acid present in the acid sodium formate is undesirable, owing to its corrosive action.

In the field of animal nutrition, sodium diformate offers the advantage that the trace element sodium need not be added separately in the form of NaCl as otherwise customary, but already represents a sodium source as such. Owing to the high formic acid content in sodium diformate, e.g. compared with trisodium hydrogentetraformate, the content of sodium ions is limited. A low or limited content of cations, e.g. including potassium ions, is desirable to the extent that the latter in particular in the case of monogastric animals and especially in the case of poultry can lead to an increased liquid intake (increased drinking) and thus to dilution of the excreta of the animals, that is to say can develop diuretic activity.

The object underlying the present invention was to provide a simple and inexpensive process for producing a solid sodium diformate preparation which essentially consists of sodium diformate and is preferably in as stable, dry, and pure a form as possible, which process avoids the above-described problems from the prior art. In particular, recirculation of the mother liquor to the production process should be enabled in such a manner that no separate concentration or drying step is required for the ejection of excess water and/or without excess sodium formate arising. The inventive process should, furthermore, enable the production of such a preparation which has a high formic acid content and in which the sodium diformate is present in high purity and also in comparatively stable and dry form, so that the process is applicable in the context of an industrial production, in particular at comparatively low temperatures.

This object has surprisingly been achieved by crystallizing out the target compound from a mixture of sodium formate with a more than one and a half times molar excess of formic acid while maintaining a molar ratio of formic acid to water of at least 1.1:1, feeding the mother liquor at least in part to a distillation apparatus (DV) and obtaining the solution to be crystallized in or downstream of the distillation apparatus (DV), excess water essentially only being ejected by removal from the distillation apparatus (DV).

The present invention therefore firstly relates to a process for producing a solid sodium diformate preparation having a formic acid content of at least 35% by weight based on the total weight of sodium diformate preparation, in which, at elevated temperature, an aqueous solution (E) is produced which comprises sodium formate and formic acid in a molar ratio of HCOOH:HCOONa of greater than 1.5:1 and which has a molar ratio of HCOOH:H$_2$O of at least 1.1:1, the aqueous solution (E) is brought to crystallization to obtain a solid phase (F) and a mother liquor (G), and the solid phase (F) is separated off from the mother liquor (G), (wherein the aqueous solution (E) is prepared according to steps (i) to (iv))

(i) the mother liquor (G), in total or partially, being fed to a distillation apparatus (DV);
(ii) the mother liquor (G) in the distillation apparatus (DV) being admixed with a sodium-comprising base (A) to obtain a mixture (B) comprising sodium formate and formic acid;
(iii) admixing the mixture (B) obtained from step (ii) with formic acid (D) to obtain the aqueous solution (E); and
(iv) excess water (C) essentially being ejected only by withdrawal from the distillation apparatus (DV).

The skilled person will readily appreciate that in order to carry out the inventive process, steps (i) to (iv) need not necessarily be followed in a chronological order. Rather, two or more of steps (i) to (iv) may also be carried out simultaneously, particularly in the case where the inventive process is run continuously. Thus, as step (iv) is explicitly locally connected to the distillation apparatus (DV), step (iv) will usually be carried out e.g. simultaneously with step (ii) or directly after step (ii) has been performed. Hence, step (iv) may particularly be carried out before step (iii) is carried out.

The inventive process enables, in an economical manner, with minimized expenditure on apparatus, simple and inexpensive production of a solid dry sodium diformate preparation which is as stable as possible, on an industrial scale. In particular, surprisingly, despite the high salt loading on operating the distillation apparatus (DV) with maintenance of the inventive production parameters, solids deposits and incrustations are substantially avoided. A further advantage is the low water content which can be set in a simple manner in the aqueous solution (E) which is brought to crystallization. By crystallizing the sodium diformate at low water contents, e.g. at less than 10% by weight, based on the aqueous solution (E), elevated crystallization temperatures and also elevated yields at a fixed final temperature can be achieved.

The inventive sodium diformate preparations are customarily obtained by preparing the aqueous solution (E) in a crystallization stage (KS), which aqueous solution (E) essentially comprises sodium formate, formic acid and water in the above described ratios, in particular as sole constituents. In the crystallization stage (KS), the solid phase (F) is crystallized out from the aqueous solution (E), an aqueous suspension (S) comprising the mother liquor (G) and the solid phase (F) being obtained. The solid phase (F) and the mother liquor (G) of the suspension (S) are then separated from one another in a separation stage (TS) by means of a conventional solid-liquid phase separation. The inventive sodium diformate preparations are obtained in this way, generally downstream of a drying step.

The aqueous solution (E) has a specific composition as specified above, i.e. it essentially comprises sodium formate, formic acid and water in the above described ratios. For the purpose of the present invention, however, it is to be noted that, while the aqueous solution (E) may already comprise sodium formate, formic acid and water in the above described ratios, the composition of the aqueous solution (E) may nonetheless vary during the inventive process within said above described ratios, the resulting reaction mixture also being termed aqueous solution (E). In particular, this may apply in process steps wherein water is removed from the reaction system and/or wherein a subquantity (G*) withdrawn from the mother liquor (G) is recycled to the reaction system, more particularly to the aqueous solution (E) obtained from step (iii).

The formic acid used is commercially available and can be used as such without pretreatment. Customarily, use is made of an aqueous formic acid solution having a formic acid content of at least 74% by weight, in particular at least 80% by weight, or preferably a concentrated formic acid. A concentrated formic acid is taken to mean by a person skilled in the art a formic acid solution having a formic acid content of 94% by weight or more, i.e. having a residual water content of less than 6% by weight, in each case based on the total weight of the formic acid solution. Aqueous formic acid designates a solution of formic acid in water having a formic acid content of less than 94% by weight, based on the total weight of the aqueous formic acid solution. The aqueous formic acid solution used preferably has a concentration of at least 80% by weight, particularly preferably at least 85% by weight, and very particularly preferably at least 90% by weight. In particular, use is made of concentrated formic acid having a formic acid content of at least 94% by weight. The concentration of the formic acid or formic acid solution may in particular not exceed 99% by weight, and is preferably in the range from 80 to 99% by weight, particularly preferably in the range from 85 to 99% by weight, and very particularly preferably in the range from 94 to 98% by weight.

Generally, the formic acid (D) fed in step (iii) has a water content such that the resultant aqueous solution (E) has a water content of at most 25% by weight, in particular at most 20% by weight, and especially at most 15% by weight, in each case based on the total weight of the aqueous solution (E). Frequently, the water content of the formic acid (D) is such that the resultant aqueous solution (E) has a water content in the range from 1 to 25% by weight, in particular in the range from 3 to 20% by weight, and especially in the range from 5 to 15% by weight, in each case based on the total weight of the mixture (B).

The sodium formate required for preparing the aqueous solution (E) is firstly introduced via the recirculated mother liquor (G), and if appropriate (G*) into the production process. If desired, a subquantity (G*), e.g. in the range from 10 to 90% by weight, and in particular in the range from 20 to 80% by weight, based on the total weight of the mother liquor (G), can be withdrawn from the mother liquor (G) downstream of removal of the solid phase (F). Preferably, the amount of the withdrawn subquantity (G*) will not exceed 75% by weight, more preferably not exceed 50% by weight, and in particular will be less than 30% by weight, e.g. in the range from 5 to 75% by weight, in particular in the range from 5 to 50% by weight, more particularly in the range from 5 to 30% by weight based, in each case on the total weight of the mother liquor (G).

The withdrawn subquantity (G*), in total or partially, may be used in production of the aqueous solution (E), e.g. by feeding it to the crystallization stage (KS), if appropriate after mixing with the stream (E), respectively, withdrawn from the distillation apparatus (DV), see FIG. 3. In one embodiment, the withdrawn subquantity (G*) is used in total in production of the aqueous solution (E). In another embodiment, the withdrawn subquantity (G*) is used partially in production of the aqueous solution (E). The amount of the withdrawn subquantity (G*) which is partially used in production of the aqueous solution (E) may be e.g. in the range from 1 to 99% by weight, and in particular in the range from 5 to 95% by weight, based in each case on the total weight of the withdrawn subquantity (G*).

In a preferred embodiment, the subquantity (G*) is used partially in production of the aqueous solution (E), while the remaining part (J) of the subquantity (G*) may be purged or may be used in production of a sodium-comprising base (A), such as sodium formate, see FIG. 3. In this case, the amount of the remaining part (J) of the subquantity (G*) may be e.g. in the range from 1 to 99% by weight, and in particular in the range from 5 to 95% by weight, based in each case on the total weight of the withdrawn subquantity (G*).

In another preferred embodiment, a subquantity (G*) is taken off from the mother liquor (G) such that, together with the remaining amount of mother liquor (G), as much formic acid is recirculated to the distillation apparatus (DV) that, by means of neutralization by the sodium-comprising base (A), again, such an amount of sodium formate is prepared as was previously ejected from the process by the stream (F) in the form of sodium diformate.

The fraction of sodium formate further required can be prepared by partial or substantially complete neutralization of the formic acid present in the recirculated mother liquor (G), and/or can be fed directly into the distillation apparatus (DV). In the former case, the sodium-comprising base (A) used for the neutralization is selected from sodium hydroxide, sodium carbonate, sodium hydrogencarbonate, sodium $C_1$-$C_6$-alkanoates, such as sodium methanolate, ethanolate, propanolate, butanolate, pentanolate and hexanolate, and mixtures thereof. In the latter case, sodium formate is used as sodium-comprising base (A). Preferably, the base (A) is selected from sodium formate, sodium hydroxide, sodium carbonate and mixture thereof, particularly preferably from sodium formate and sodium hydroxide. By mixing the sodium-comprising base (A) and the mother liquor (G) in step (ii), the mixture (B) comprising sodium formate and formic acid is obtained.

The sodium-comprising base (A) can be fed to the distillation apparatus (DV) in step (ii) in the form of, e.g. an aqueous solution or suspension, or else as solid. Preference is given to feed in the form of an aqueous solution or suspension. For this, use can be made of, e.g., a 30 to 60% strength by weight sodium hydroxide solution, a 30 to 60% strength by weight sodium carbonate solution, or a mixture thereof, or a 30 to 60% strength by weight sodium formate solution. Generally, the sodium-comprising base (A)-comprising aqueous solution or suspension has a water content in the range from 10 to 80% by weight; in particular in the range from 20 to 70% by weight, and especially in the range from 30 to 60% by weight, in each case based on the total weight of the aqueous solution or suspension.

In a preferred embodiment, as sodium-comprising base (A), use is made of NaOH in the form of an aqueous sodium hydroxide solution which has an NaOH content in the range from 20 to 90% by weight, particularly preferably in the range from 30 to 80% by weight, and very particularly preferably in the range from 40 to 70% by weight, in each case based on the total weight of the aqueous sodium hydroxide solution.

In a further preferred embodiment, as sodium-comprising base (A), use is made of sodium formate in the form of an aqueous solution or suspension which comprises sodium formate in an amount in the range from 20 to 90% by weight, particular preferably in the range from 30 to 80% by weight, and very particularly preferably in the range from 40 to 70% by weight, based on the total weight of the sodium formate solution or suspension.

The sodium formate used as sodium-comprising base (A) can be, e.g. technical sodium formate. Sodium formate obtained in the production of polyols as waste product is also suitable for use in the present invention. In this case, if appropriate a partial ejection of mother liquor is required, since in polyol synthesis, high-boiling organic components are also obtained. It is likewise possible to produce the sodium formate to be used, e.g. by reacting sodium hydroxide, carbonate or hydrogencarbonate with formic acid, by reacting carbon monoxide with liquid sodium hydroxide, or by reacting methyl formate with sodium hydroxide. In the case of this variant, a procedure can be followed, e.g., such that solid NaOH or a concentrated aqueous solution thereof, if appropriate with cooling and/or stirring, is dissolved in the preferably concentrated formic acid. The sodium formate can be crystallized in this case by temperature reduction and/or decreasing the water content of the mixture by customary processes known to those skilled in the art, e.g. evaporation, extraction, distillation and the like, or the freshly made up, or if appropriate temporarily stored, sodium formate solution or suspension is being used as such. The crystallization conditions for sodium formate are known to those skilled in the art and described, e.g., in Zagidullin, S. K., et al., "Investigation of Supersaturations in the Sodium Formate—Water System to Optimize Crystallization", Russian Journal of Applied Chemistry, Vol. 69 (1996), 5, 669-672. For example, evaporation crystallization or cooling crystallization using wall cooling or evaporative cooling can be carried out. It has been noted that at low temperatures, e.g. at lower than 30° C., particularly lower than 20° C., hydrate forms of the sodium formate which comprise more than one $H_2O$ molecule bound as crystal water per sodium formate unit can crystallize out. This is generally undesirable and is therefore to be avoided by crystallization at higher temperatures.

Generally, use is made of a sodium formate whose HCOONa content is at least 97% by weight, based on the total weight of the sodium formate source used. Preferably, use is made of a sodium formate which comprises less than 0.1% by weight, and in particular less than 0.05% by weight, in each case based on the total weight of the sodium formate source used, of potassium ions. If no mother liquor is yet available, as is the case, e.g., before the first running of the process, the abovementioned sodium formate sources first serve as sole sodium formate source until mother liquor (G) or (G*) is available.

It has proved to be advantageous to admix the mother liquor (G) in step (ii) with an amount of the sodium-comprising base (A)-comprising aqueous solution or suspension such that the resultant mixture (B) has a water content of at most 20% by weight, in particular at most 15% by weight, and especially at most 12% by weight, in each case based on the total weight of the mixture (B). Frequently, use is made of the sodium-comprising base (A)-comprising aqueous solution or suspension in an amount such that the water content of the resultant mixture (B) is in the range from 1 to 20% by weight, in particular in the range from 3 to 15% by weight, and especially in the range from 5 to 12% by weight, in each case based on the total weight of the mixture (B).

In addition, it has proved to be advantageous to admix, in step (ii), the mother liquor (G) with an amount of the sodium-comprising base (A) such that the molar ratio of HCOOH:HCOONa in the resultant mixture (B) is in the range from 1:1 to 2:1, and in particular in the range from 1.2:1 to 1.8:1.

Generally, in steps (i) and (ii), the weight ratio of the sodium-comprising base (A)-comprising aqueous solution or suspension to the mother liquor (G) which is fed in each case to the distillation apparatus (DV) is in the range from 2:1 to 1:6, and in particular in the range from 1:1 to 1:3.

According to the invention, in step (iii), the mixture (B) obtained from step (ii) is admixed with formic acid (D) to obtain the aqueous solution (E). In this connection the formic acid (D) can be added to the mixture (B) either directly in the distillation apparatus (DV), or else after withdrawal of the mixture (B) from the distillation apparatus (DV). In the latter case, the formic acid (D) can be added before or after the mixture (B) has been fed to the crystallization stage (KS). It is obvious to a person skilled in the art that in this case it is also possible to add the mixture (B) to the formic acid (D) which is present. By mixing the formic acid (D) and the mixture (B) the aqueous solution (E) is thus obtained either in the distillation apparatus (DV), after withdrawal of the mixture (B) from the distillation apparatus (DV) and before feeding thereof to the crystallization stage (KS), or firstly in the crystallization stage (KS).

The respective material streams are preferably set in such a manner that the aqueous solution (E) comprises formic acid in an amount of at least 1.6 mol, particularly preferably at least 1.7 mol, and very particularly preferably at least 1.8 mol, of HCOOH per mole of HCOONa. Preferably, the molar ratio of HCOOH:HCOONa in the aqueous solution (E) is in the range from 1.6:1 to 3:1, particularly preferably in the range from 1.7:1 to 2.5:1, and very particularly preferably in the range from 1.8:1 to 2.3:1.

The respective material streams are, in addition, preferably set in such a manner that the molar ratio of $HCOOH:H_2O$ in the aqueous solution (E) is at least 1.5:1, and particularly preferably at least 1.8:1; very particularly preferably, it is in the range from 1.5:1 to 10:1, and in particular in the range from 1.8:1 to 6.1:1.

The distillation apparatus (DV) used in the inventive process is preferably a distillation column selected from tray columns, columns having fixed internals, random-packing columns and ordered-packing columns. Preferably, use if made of a tray column, e.g. a bubble-cap tray column. If in the distillation apparatus (DV) reactive distillation is carried out, e.g. when using sodium-comprising bases (A) such as sodium hydroxide, sodium carbonate, or sodium hydrogencarbonate, then preferably use is made of holdup time trays, e.g. Thormann trays. Particularly preferably, use is made of a tray column, in particular a bubble-cap tray column having a number of trays in the range from 10 to 40, and in particular in the range from 20 to 30.

The reflux ratio in the distillation apparatus (DV), in particular in the distillation column, and especially in the tray column, is set in particular to a value in the range from 0 to 5. Customarily, the pressure in the distillation apparatus (DV) will be in the range from 100 to 1500 mbar, and in particular in the range from 200 to 1000 mbar. Generally, the temperature in the distillation apparatus (DV) is in the range from 60 to 200° C. In particular, the temperature in the distillation apparatus (DV) is in the range from 60 to 160° C.; a temperature of 160° C. will generally only be exceeded in the bottom. In particular especially when the formic acid (D) is also being fed into the distillation apparatus (DV) or into the distillation column, the temperature being established in the bottom of the distillation apparatus (DV) or the distillation column is of importance. The latter is frequently in the range from 80 to 200° C., in particular in the range from 95 to 140° C., and especially in the range from 100 to 135° C.

The procedure of the inventive process is described hereinafter by way of example using a tray column, e.g. a bubble-cap tray column, having a number of trays in the range from 20 to 30. Of course, for a person skilled in the art, the process illustrated in this manner can be applied to other types of distillation apparatuses (DV), in particular other types of distillation columns. Adaptations required for this if appropriate of individual process parameters can be determined by a person skilled in the art without problems on the basis of his or her specialist knowledge and/or by routine experiments.

Generally, a procedure is followed such that, in step (i), the mother liquor (G) is fed in the lower region, e.g. in the lower third, or lower quarter, of the distillation apparatus (DV). It has proved advantageous in this case to feed the mother liquor (G) approximately in the region of the lower 8 trays, e.g. in the region between the bottom and the seventh tray.

Usually, in step (ii), the sodium-comprising base (A) is fed at the top of the distillation column (DV). It has proved advantageous to feed the sodium-comprising base (A) approximately in the region of the upper 4 trays, e.g. in the region of the top tray. Mixing the sodium-comprising base (A) and the mother liquor (G) in step (ii) produces the sodium-formate- and formic-acid-comprising mixture (B) in the distillation column (DV).

According to the invention, water (C) not required for producing the aqueous solution (E), i.e. excess water, is essentially ejected only by withdrawal from the distillation column (DV) (step (iv)). Small amounts of water which can adhere to the solid phase (F) obtained in the separation stage (TS) are ejected from the process together with the latter. It has proved advantageous, in step (iv), to eject the water (C) at the top of the distillation column (DV), in particular in the region of the upper 3 trays; e.g. in the region of the top tray or there above. Generally, the water (C) is ejected above the feed of the sodium-comprising base (A). The water (C) thus discharged comprises, if appropriate, small fractions of formic acid. These are generally only present as traces in the discharged water (C), e.g. in an amount of no greater than 0.5% by weight, and in particular no greater than 0.25% by weight, based on the total weight of the discharge (C).

As described above, in step (iii), the formic acid (D) can be added to the mixture (B) either directly in the distillation column (DV) or else after withdrawal of the mixture (B) from the distillation column (DV), in each case the aqueous solution (E) being obtained according to the invention.

According to the invention, the mixing of the formic acid (D) and the mixture (B), where this is not performed in the distillation column (DV), can be carried out in all apparatuses customarily used for the purpose of producing a homogeneous liquid mixture, such as reactors, kettles, flasks etc., in particular in stirred vessels, especially those having internal heat exchange surfaces. These are known to those skilled in the art. To avoid corrosion effects, e.g. in reactors or kettles made of steel, it is advantageous if the surfaces and walls coming into contact with formic acid are coated with an acid-resistant protecting layer, e.g. of Teflon®, or are lined with especially acid-resistant high-alloy steels. It is obvious to a person skilled in the art that these statements apply equally to the remaining plant components for carrying out the inventive process, in particular to the distillation column (DV), the crystallization stage (KS), and also the separation stage (TS).

In a preferred embodiment, in step (iii), the mixture (B) obtained from step (ii) is taken off from the distillation column (DV), the mixture (B) is admixed with formic acid (D) to obtain the aqueous solution (E), and the resultant aqueous solution (E) is fed to a crystallization stage (KS) (see FIG. 1). The mixture (B) is taken off from the distillation column (DV) in the lower region of the distillation column (DV), e.g. in the region of the lower 5 trays, in particular in the region below the first tray, and especially at the bottom.

In a further preferred embodiment, in step (iii), the formic acid (D) is fed in the lower region of the distillation column (DV) comprising the mixture (B); the aqueous solution (E) obtained in this manner at the bottom of the distillation column (DV) is then fed to a crystallization stage (KS) (see FIG. 2). In this case the formic acid (D) is fed markedly beneath the feed of the sodium-comprising base (A), e.g. in the region of the lower 8 trays, and in particular in the region of the lower 5 trays. In particular, the formic acid (D) is fed below the feed of the mother liquor (G).

In a further preferred embodiment, in step (iii), the mixture (B) obtained from step (ii) is taken off from the distillation column (DV), the mixture (B) is fed to the crystallization stage (KS) and it is admixed with the formic acid (D) in the crystallization stage (KS) to obtain the aqueous solution (E). The mixture (B) is taken off from the distillation column (DV) in the lower region of the distillation column (DV), e.g. in the region of the bottom 5 trays, in particular in the region below the first tray, and especially at the bottom.

Particularly preferably, the aqueous solution (E) and the mixture (B) are each taken off in the region below the first tray, in particular at the bottom of the distillation column (DV).

The aqueous solution (E) or the mixture (B) is fed to the crystallization stage (KS). In the latter case, the formic acid (D) is also fed directly to the crystallization stage (KS), the aqueous solution (E) being obtained in the crystallization stage (KS). If appropriate, the subquantity (G*) taken off from the mother liquor (G) is additionally fed to the crystallization stage (KS). The aqueous solution (E) is generally a homogeneous liquid mixture of the starting materials formic acid, sodium formate and water required for crystallization of sodium diformate. It is essential to the invention in this connection that the molar ratios of these starting materials defined above for producing the aqueous solution (E) are adhered to.

According to the invention, the aqueous solution (E) is produced or prepared for crystallization at elevated temperature, with a distinction needing to be made between these two aspects. For instance, the production of the aqueous solution (E), if appropriate being performed in the distillation column (DV), can be performed at relatively high temperatures, e.g. at the temperatures stated above for operation of the distillation apparatus (DV). When the aqueous solution is prepared for crystallization in the crystallization stage (KS), in contrast, the temperatures are generally lower, e.g. at least 30° C., in particular at least 40° C., and especially at least 50° C., with generally 100° C., in particular 80° C., and especially 70° C., not being exceeded. If, during preparation of the starting materials in the crystallization stage (KS), a homogeneous and liquid aqueous solution is not attained directly, for instance because not all components are completely dissolved, the reaction mixture is converted into the aqueous solution (E) by elevating the temperature, preferably with stirring.

The temperature of the reaction mixture, e.g. in the distillation column (DV) and in the crystallization stage (KS) is set by conventional methods, e.g. by adjusting the addition rate(s) and/or cooling or heating of the mixture and/or of the added solution(s) and/or suspension(s). Generally, the temperature in the crystallization stage (KS) is set before the start of crystallization in such a manner that a temperature in the range from 30° C. to 80° C., and in particular from 40° C. to 70° C., is present in the reaction mixture. Preferably, the temperature of the mixture is not above 65° C. It is critical to the invention that the crystallization is performed from an aqueous solution. It is possible, as explained in more detail hereinafter, that this is admixed, or for this to be admixed, with seed crystals even before the start of the crystallization.

In the crystallization stage (KS), the reaction mixture is advantageously agitated, e.g. stirred. The agitation is continued at least until the completely homogeneous aqueous solution (E) is obtained, generally until the end or termination of the crystallization.

According to the invention, the aqueous solution (E) is brought to crystallization, preferably under continued stirring. This can be achieved, e.g. by partial evaporation or by cooling, preferably by cooling. If the crystallization is achieved or initiated or accelerated by controlled evaporation of the liquid phase, preferably under vacuum, it must be ensured that the molar ratios of the components in the solution (E) are within the above specified ranges at the start of crystallization. If the crystallization is achieved by cooling, this is preferably performed slowly, advantageously over a period of one to a plurality of hours, e.g. up to 24 h, or up to 12 h, in particular from 1 to 15 h, and especially from 2 to 10 h. In this case sodium diformate crystallizes out. It has proved to be advantageous if the cooling is performed at a cooling rate in the range from 2 to about 20 K/h, e.g. about 5 to 15 K/h. To achieve thorough crystallization of the target compound, it is advantageous to cool the aqueous solution in said period to a temperature of below 30° C., e.g. about 25, 20, 15 or 10° C., or below. Generally in this case, the temperature does not fall below 0° C., and in particular 5° C.

It has proved to be advantageous, after initiation of crystal formation, to dissolve the crystal nuclei or small crystals first formed by heating, e.g. to a temperature of a maximum 65° C., in particular in the range from 25° C. to 50° C., and then to start the crystallization process again by further, if appropriate slow, cooling. In this further cooling, the rate is customarily in the range from about 0.5 to 20 K/h, e.g. at about 1 to 15 K/h, in particular at about 2 to 15 K/h, especially at about 5 to 10 K/h. Preferably, the cooling rate will not exceed a maximum of 25 K/h. The crystallization temperature is in the ranges mentioned above.

In addition, it can be advantageous to add, to the aqueous solution (E), preexisting crystals of sodium diformate, e.g. crystals of sodium diformate produced in advance by the inventive process to promote the crystallization process, i.e. for the purpose of what is termed "seeding". Such crystals can be added in dry or moist form, suspended in a liquid, e.g. aqueous or formic acid phase, or a combination of these forms. In this case the addition is generally performed above a temperature which leads to crystal formation, but below a temperature at which the crystals dissolve to form a completely homogeneous solution. The temperature of the reaction mixture on addition of crystals will therefore generally not exceed 65° C., and preferably be in the range from 25 to 50° C. The crystallization process can then be performed, as described above, at a cooling rate in the range from about 0.5 to about 20 K/h, e.g. about 1 to 15 K/h, in particular about 2 to 15 K/h, and especially about 5 to 10 K/h. The crystallization temperature is in the ranges mentioned above.

In a preferred embodiment, the crystallization is carried out continuously. For this, in the solution to be crystallized, or in the crystallization stage (KS) a constant temperature is maintained at which crystallization takes place, e.g. 25° C. or below, in particular in the range from 0 to 20° C., and especially in the range from 5 to 15° C., e.g. about 10° C. Since, at such temperatures, crystal formation always occurs, seeding in this case is generally not necessary.

Subsequent to the crystallization, the resultant solid phase (F) is separated off from the mother liquor (G). Separation of the solid phase (F) from the mother liquor (G) generally comprises a drying step. In a preferred embodiment, the solid phase (F) is separated off from the mother liquor (G), and the solid phase (F) thus obtained is dried to obtain the solid sodium diformate preparation of the present invention.

The solid phase (F) is advantageously separated off from the mother liquor (G) in a separate separation stage (TS). For this, conventional processes are known to those skilled in the art, e.g. filtration or centrifugation, preferably centrifugation, in particular using pusher-type or peeler centrifuges. The moist sodium diformate preparation thus obtained (solid phase (F)) generally still comprises small amounts of formic acid, water and/or sodium formate. The formic acid content in this still-moist sodium diformate preparation is customarily greater than 40.3% by weight, and in particular in the range from 40.7 to 42.5% by weight, based on the total weight of the moist preparation.

The moist product (solid phase (F)) is then dried by customary drying processes, e.g. under vacuum and/or moderate heating. Dryers and drying processes which are usable for this are known to those skilled in the art and are described, e.g., in K. Kröll, Trockner und Trocknungsverfahren [Dryers and drying processes], 2nd Edition, Springer Verlag, Berlin 1978. In particular, use can be made of, e.g. contact dryers, fluidized-bed dryers and jet dryers, if appropriate spray dryers. The relative high volatility of the formic acid present in the product and also the limited temperature stability of the product must be taken into account in this case. During drying, generally, a product temperature of 65° C., and in particular 50° C., will not be exceeded. The water content remaining in the product after drying (residual water content) is generally no greater than 0.5%, and is customarily in the range from about 0.5 to 0.01% by weight, preferably at most 0.3% by weight, particularly preferably at most 0.2% by weight, and very particularly preferably at most 0.1% by weight, based on the total weight, determined by oxidimetric titration according to Karl Fischer (e.g. described in Wiland, Wasserbestimmung durch Karl-Fischer-Titration [Water determination by Karl-Fischer titration], Darmstadt, GIT, 1985).

Here and hereinafter, the expression total weight of the sodium diformate preparation is used synonymously with the expression total dry weight. The total dry weight is to be taken to mean the weight of the sodium diformate preparation which is yielded by drying the product below its decomposition temperature, e.g. by drying over a period of 1 h at a temperature of 35° C. and a pressure of 50 mbar.

To carry out the inventive process it is advantageous to achieve as high a yield as possible in the crystallization of the sodium diformate, because as a result the internal material streams can be minimized. As a result the expenditure on apparatus can be reduced, in that, e.g., the apparatuses used can be dimensioned to be smaller.

If a subquantity (G*) is taken off from the mother liquor (G) obtained from the separation stage (TS), this subquantity (G*) may be used, preferably as solution in unprepared form, in production of the aqueous solution (E), e.g. by feeding it directly to the crystallization stage (KS). Alternatively, the subquantity (G*) may be admixed with the aqueous solution (E) obtained from step (iii) before being fed to the crystallization stage (KS). Obviously, it can also be temporarily stored in conventional vessels such as tanks or kettles and used as required at a later time point to produce the aqueous solution. In this case, the subquantity (G*) is used, e.g. as solution or suspension. Furthermore, the subquantity (G*), in total or partially, may be purged or used in production of a sodium-containing base (A).

In a preferred embodiment, a procedure is followed in such a way that a) a sodium-comprising base (A)-comprising aqueous solution or suspension is fed at the top of the distillation apparatus (DV), in particular a distillation column as described above;

b) the mother liquor (G) is fed in the lower region of the distillation apparatus (DV), the sodium-formate- and formic acid-comprising mixture (B) being obtained;

c) the water (C) is ejected at the top of the distillation apparatus (DV);

d) the mixture (B) from step b) is taken off at the bottom of the distillation apparatus (DV) and admixed with the formic acid (D) to obtain the aqueous solution (E);

e) the aqueous solution (E) obtained from step d) is fed to a crystallization stage (KS) and herein brought to crystallization to obtain the suspension (S) comprising the solid phase (F) and the mother liquor (G); and f) the suspension (S) from step e) is fed to a separation stage (TS) in which the solid phase (F) is separated off from the mother liquor (G), moist sodium diformate being obtained as solid phase (F).

A diagram of the process corresponding to this preferred embodiment is reproduced in the accompanying FIG. 1. The stream (D) can be mixed with the steam (B) in step d)

upstream or downstream of feed to the crystallization stage, e.g. upstream of the feed as shown in such a manner that the stream (D) is fed to the stream (B). Obviously, the stream (B) can alternatively be added to the stream (D), or both streams (B) and (D) can be fed separately to the crystallization stage and not mixed with one another until they are there.

In a further preferred embodiment, a procedure is followed in such a way that aa) a sodium-comprising base (A)-comprising aqueous solution or suspension is fed at the top of the distillation apparatus (DV), in particular a distillation column as described above;

bb) the mother liquor (G) is fed in the lower region of the distillation apparatus (DV), the sodium-formate- and formic acid-comprising mixture (B) being obtained;

cc) the water (C) is ejected at the top of the distillation apparatus (DV);

dd) the mixture (B) from step bb) is admixed with the formic acid (D) in the distillation apparatus (DV) to obtain the aqueous solution (E);

ee) the aqueous solution (E) obtained from step dd) is taken off at the bottom of the distillation apparatus (DV), fed to a crystallization stage (KS) then brought to crystallization to obtain the suspension (S) comprising the solid phase (F) and the mother liquor (G); and ff) the suspension (S) from step ee) is fed to a separation stage (TS) in which the solid phase (F) is separated off from the mother liquor (G), moist sodium diformate being obtained as solid phase (F).

A diagram of the process corresponding to this preferred embodiment is reproduced in the accompanying FIG. 2.

In a particularly preferred embodiment of the two above described process variants (steps a) to f), and steps aa) to ff), respectively), a procedure is followed in such a way that, in addition, g) a subquantity (G*) is taken off from the mother liquor (G) obtained from the separation stage (TS) in step f) or ff), and the withdrawn subquantity (G*) is fed to the crystallization stage (KS).

In another particularly preferred embodiment of the two above described process variants (steps a) to f), and steps aa) to ff), respectively), a procedure is followed in such a way that, in addition, g') a subquantity (G*) is taken off from the mother liquor (G) obtained from the separation stage (TS) in step f) or ff), the withdrawn subquantity (G*), in total or partially, being used in production of the aqueous solution (E).

In step g'), the withdrawn subquantity (G*), in total or partially, may be admixed with the aqueous solution (E) before introduction into the crystallization stage (KS). Alternatively, the withdrawn subquantity (G*), in total or partially, may be directly introduced into the crystallization stage (KS). If appropriate, the remaining part (J) of the withdrawn subquantity (G*) may be purged or may be used in production of a sodium-comprising base (A), such as sodium formate.

A diagram of the process corresponding to the two aforementioned particularly preferred embodiments (involving either step g) or step g*) is reproduced in the accompanying FIG. 3.

In still another particularly preferred embodiment of the two above described process variants (steps a) to f), and steps aa) to ff), respectively), a procedure is followed in such a way that, in addition, g") a subquantity (G*) is taken off from the mother liquor (G) obtained from the separation stage (TS) in step f) or ff), the withdrawn subquantity (G*) being purged or being used in production of the sodium-containing base (A).

With respect to the above preferred embodiments comprising the steps a) to f) and g),
a) to f) and g'),
a) to f) and g"),
aa) to ff) and g),
aa) to ff) and g'), or
aa) to ff) and g"), in each case the individual parameter ranges extensively described above in general form, including their preferred ranges, apply.

The inventive process can be carried out continuously, semicontinuously, or batchwise.

The solid sodium diformate preparation is obtained by the inventive process in high purity and has, therefore, after drying a high content of formic acid, generally at least 35% by weight, frequently at least 36% by weight, in particular at least 37% by weight, especially at least 38% by weight, very especially at least 39% by weight, and still more especially at least 40% by weight, in each case based on the total weight of the sodium diformate preparation. Generally, the formic acid content in the inventively obtained sodium diformate preparation will be no more than 41% by weight, and in particular no more than 40.5% by weight, in each case based on the total weight of the solid sodium diformate preparation. Especially, the content is in the range from 38 to 41% by weight, very especially in the range from 39 to 40.5% by weight, and still more especially in the range from 40 to 40.3% by weight, in each case based on the total weight of the obtainable sodium diformate preparation. The formic acid content in the dry product can be determined in a conventional manner, e.g. by titration of the formic acid with a base. Of course, a high content of formate anions is likewise present in the dry product.

The inventively obtained sodium diformate preparation is typically obtained in crystalline form. It is assumed that the preparation corresponds essentially or completely to the formula HCOONa.HCOOH (sodium diformate), which, however, is not to be understood as a limitation of the invention. Rather, it is essential to the invention that the preparation comprises sodium formate and formic acid in associated, crystalline form. The inventively obtained crystalline modification of the sodium formate may be identified, for example, by X-ray wide-angle scattering. Unwanted modifications, e.g. trisodium hydrogentetraformate, can likewise be detected qualitatively by the same method. The molar ratio of the components sodium formate and formic acid in the preparation is customarily in the range from 0.9: to 1.1:1; in particular in the range from 0.95:1 to 1.05:1, and corresponds especially to about 1:1. The fraction of sodium formate in the preparation is customarily at least 97% by weight, in particular at least 98% by weight, and especially at least 99% by weight, in each case based on the total weight of the preparation. As further constituents, the preparation can comprise, owing to residual moisture or crystalline residual moisture, generally up to 1.5% by weight of formic acid, up to 1.5% by weight of sodium formate and/or up to 0.5% by weight of water, in each case based on the total weight of the preparation. At about 65° C., a phase transition point may be observed by means of DSC (differential scanning calorimetry). The preparation is distinguished by a comparatively low hygroscopicity in particular compared with trisodium hydrogentetraformate. Furthermore, the inventively obtained sodium diformate preparation is sufficiently stable to ensure problem-free handling and (further) processing. In addition, the potassium ion content of the preparation obtained is generally at most 1000 ppm, and in particular at most 500 ppm, in each case based on the total weight. The chloride content due to the preparation procedure in the inventively obtained sodium formate preparation is generally less than 1500 ppm, and in particular less than 1000 ppm, in each case based on the total weight.

The inventive process for producing a solid, dry sodium diformate preparation in crystalline stable form makes it possible to apply the production conditions to an industrial scale. The process is distinguished in particular by the fact that an efficient way for ejecting water is implemented. By this means, the water content especially of the aqueous solution to be crystallized can be kept low, which is accompanied by the abovementioned advantages.

The resultant solid product can be comminuted before and/or after the drying step, e.g. by means of mortars, cutters, punch presses and rolling mills, agglomerated, e.g. by means of mixers, and/or compacted, e.g. by means of presses and compactors. The apparatuses used for such a comminution are known to those skilled in the art.

Depending on the desired purpose of use, the inventively produced sodium diformate preparation can be further processed, in particular powders of defined particle sizes can be produced, the particles produced can be covered with coatings and/or mixtures with other additives can be prepared. As examples of coatings or coating materials which may be mentioned are oils such as soybean oil, fats and fatty acids such as palmitic or stearic acid, or polymer coatings, e.g. made of polyalkylenes and derivatives thereof. Customary additives are, in particular, flow aids such as silica etc. Suitable processes for coating and also the additives coming into consideration are thoroughly known to those skilled in the art in the respective field, see, e.g. DE 102 31 891 A1.

According to the invention the sodium diformate preparation produced is in solid form, in particular as crystal powder or as granules or compactates. Depending on the application-orientated requirements, the powders, granules or compactates have a mean particle size in the range from 1 µm to 10 000 µm, in particular from 10 µm to 5000 µm, and especially from 100 µm to 2500 µm.

The inventively produced solid sodium diformate preparation and formulations and compositions comprising this are suitable for use in feeds for animals (animal feeds), in particular as additive to animal feed in the form of feed additives and especially as additive to premixes for animal feeds. Premixes are mixtures which generally comprise minerals, vitamins, amino acid, trace elements and also if appropriate enzymes. Animal feeds and feed additives which comprise the inventively prepared solid sodium diformate preparation are particularly suitable for monogastric animals such as hogs, especially piglets, breeding sows and fattening hogs, and also poultry, especially broilers, laying hens, turkeys, ducks, geese, quails, pheasants and ostriches.

Depending on the remaining substances or additives present in the feed or feed additive, the content of the inventively prepared solid sodium diformate preparation in the feed or feed additive can vary greatly. In the case of feed additives, the content furthermore depends on the type of the formulation, e.g. on the addition of additives such as desiccants, on a possible coating and on the residual moisture content. Customarily, the content of inventively produced solid sodium diformate preparation in the feed additive is, e.g. in the range from 0.1 to 99.5% by weight, in particular from 0.5 to 75% by weight, and especially from 1 to 50% by weight, based on the total dry weight of the feed additive. The inventively produced solid sodium diformate preparation is also suitable for use in a premix and can in this case be used in the customary amounts, e.g. admixed.

In particular in the case of use in animal feed and in feed additives for poultry, a small content of potassium ions is advantageous, since potassium in this case can develop a diuretic action. The use of the inventively produced sodium diformate preparation for the abovementioned purpose thus provides an acidic sodium and formate source, without necessarily the fraction of potassium ions being increased. For instance, a solid feed additive can be formulated which comprises the inventively prepared solid sodium diformate preparation and is essentially free from potassium ions. In this case essentially free from potassium ions means that the content of potassium ions is at most 1000 ppm, and in particular at most 500 ppm, in each case based on the weight of the feed additive.

Animal feeds are composed in such a way that the corresponding requirement for nutrients is optimally covered for the respective animal species. Generally, plant feed components such as corn, wheat or barley meal, whole soybean meal, soybean extraction meal, linseed extraction meal, rapeseed extraction meal, green meal or pea meal are selected as crude protein sources. To ensure an appropriate energy content of the feed, soybean oil or other animal or vegetable fats are added. Since the plant protein sources comprise some essential amino acids only in an insufficient amount, feeds are frequently enriched with amino acids. These are primarily lysine and methionine. To ensure the mineral and vitamin supply of the farm animals, in addition minerals and vitamins are added. The type and amount of added minerals and vitamins depends on the animal species and is known to those skilled in the art (see, e.g. Jeroch et al., Ernährung landwirtschaftlicher Nutztiere [Nutrition of agricultural farm animals], Ulmer, UTB). To cover the nutrient and energy requirement, use can be made of complete feeds which comprise all nutrients in a ratio to one another covering requirements. It can form the sole feed of the animals. Alternatively, a supplementary feed can be added to a grain feed of cereals. The supplement feed can comprise protein-, mineral- and vitamin-rich feed mixtures which supplement the feed.

The inventively produced solid sodium diformate preparation is suitable, in particular, as what is termed an acidifier. Acidifiers are taken to mean those substances which lower the pH. The expression comprises not only those substances which lower the pH in the substrate (e.g. animal feed), but also those which lower the pH in the gastrointestinal tract of the animal.

The inventively produced solid sodium diformate preparation is suitable in particular as a composition having performance- and/or growth-promoting effect. In a preferred embodiment, the solid sodium diformate preparation is used as such a performance- and/or growth-promoting composition for monogastric animals, in particular for hogs and/or poultry.

The inventively produced solid sodium diformate preparation is suitable, in addition, as preservative, in particular as preservative for green feeds and/or animal feeds.

The inventively produced solid sodium diformate preparation can be used advantageously in the production of silage. It accelerates lactic acid fermentation and/or prevents secondary fermentation and inhibits the development of harmful yeasts, so that they can be used as silage additives (silage aids).

Use of the inventively produced solid sodium diformate preparation as fertilizer is also possible.

DESCRIPTION OF THE FIGURES

FIG. 1 illustrates a preferred embodiment of the inventive process according to the aforementioned steps a) to f).

Figure 1:
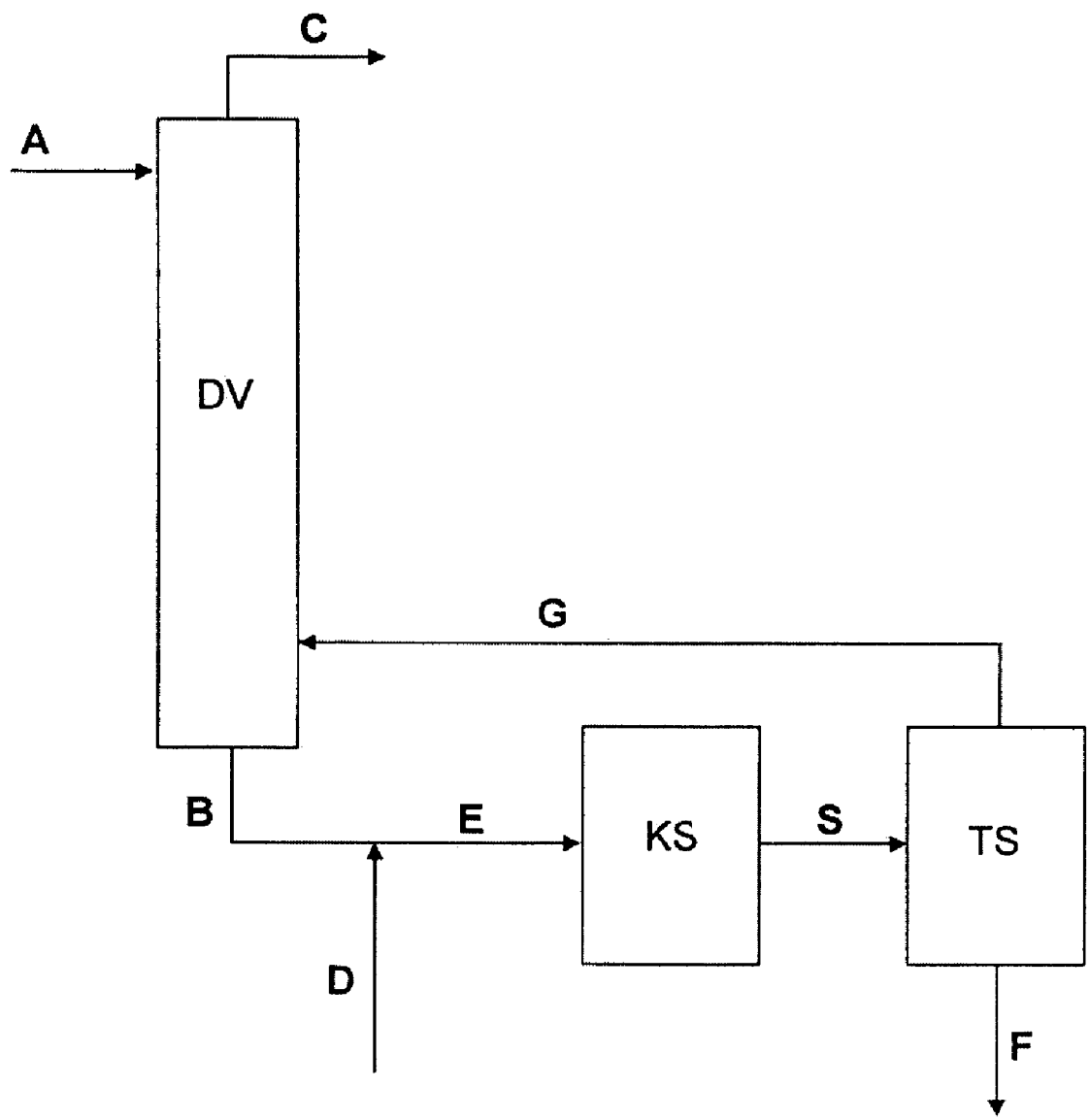
FIG. 1 shows a diagram for carrying out a variant of the inventive process. In particular.

In detail, in the process shown in FIG. 1, a procedure is followed such that a sodium-comprising base (A)-comprising aqueous solution or suspension is fed at the top to the distillation apparatus (DV), in particular of a distillation column (step a)). The mother liquor (G) is fed in the lower region of the distillation apparatus (DV), the sodium-formate- and formic-acid-comprising mixture (B) being obtained (step b)). The water (C) is ejected at the top of the distillation apparatus (DV) (step c)). The mixture (B) from step b) is taken off at the bottom of the distillation apparatus (DV) and this is admixed with the formic acid (D) to obtain the aqueous solution (E) (step d)). The aqueous solution (E) obtained from step d) is fed to a crystallization stage (KS) and this is brought to crystallization herein to obtain the suspension (S) comprising the solid phase (F) and the mother liquor (G) (step e)). The suspension (S) from step e) is fed to a separation stage (TS) in which the solid phase (F) is separated off from the mother liquor (G), moist sodium diformate being obtained as solid phase (F) (step f)). Optionally, the solid phase (F) may be dried by conventional means (not shown).

Figure 2:
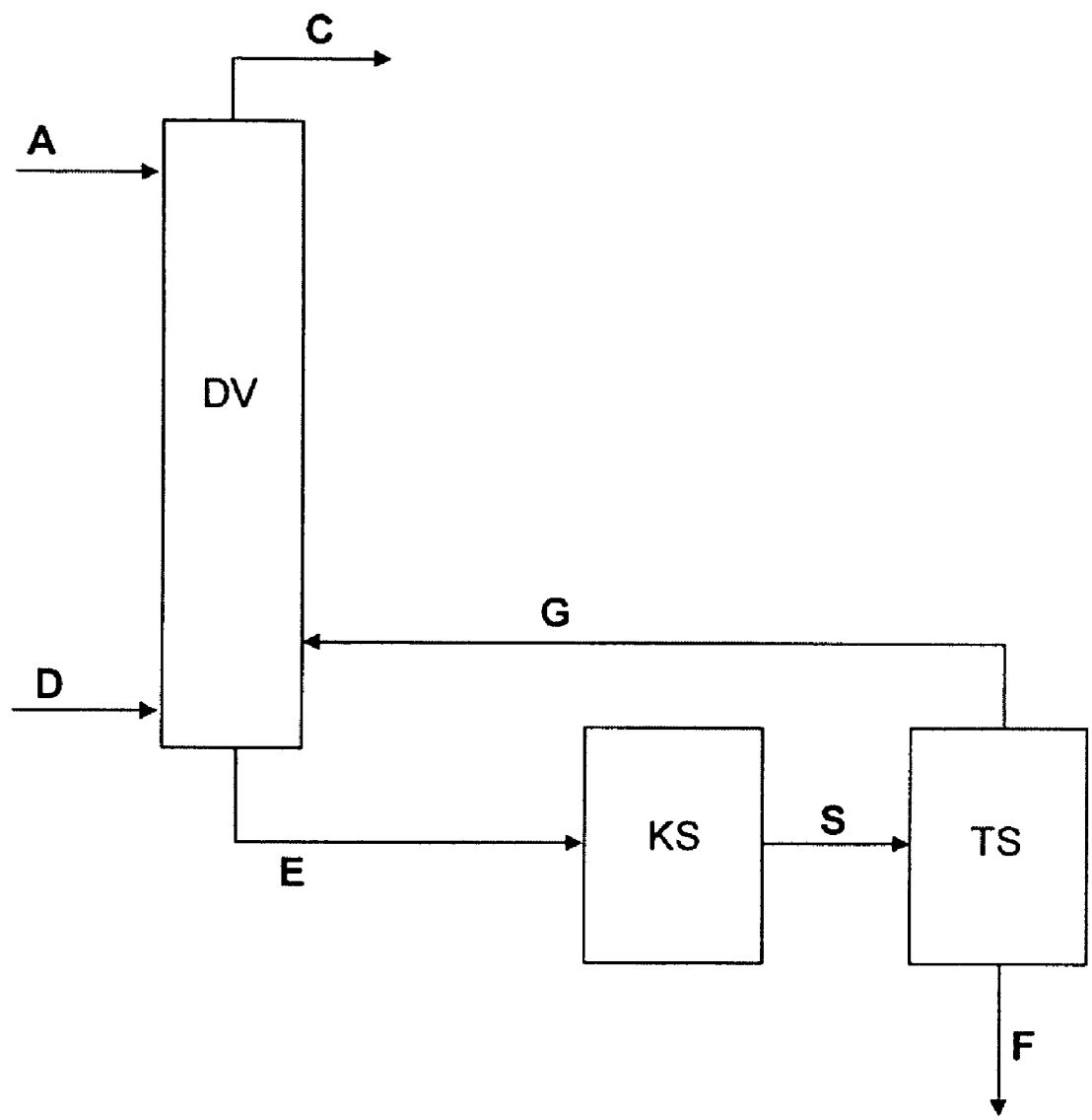

FIG. 2 shows a diagram for carrying out a further variant of the inventive process. In particular, FIG. 2 illustrates a preferred embodiment of the inventive process according to the aforementioned steps aa) to ff).

In detail, in the process shown in FIG. 2, generally a procedure is followed such that a sodium-comprising base (A)-comprising aqueous solution or suspension is fed to the top of the distillation apparatus (DV), in particular of a distillation column (step aa)). The mother liquor (G) is fed in the lower region of the distillation apparatus (DV), the sodium-formate- and formic-acid-comprising mixture (B) being obtained (step bb)). The water (C) is ejected at the top of the distillation apparatus (DV) (step cc)). The mixture (B) from step bb) is admixed with the formic acid (D) in the distillation apparatus (DV) to obtain the aqueous solution (E) (step dd)). The aqueous solution (E) obtained from step dd) is taken off at the bottom of the distillation apparatus (DV), fed to a crystallization stage (KS) and brought to crystallization herein to obtain the suspension (S) comprising the solid phase (F) and the mother liquor (G) (step ee)). The suspension from step ee) is fed to a separation stage (TS) in which the solid phase (F) is separated off from the mother liquor (G), moist sodium diformate being obtained as solid phase (F) (step ff)). Optionally, the solid phase (F) may be dried by conventional means (not shown).

Figure 3:
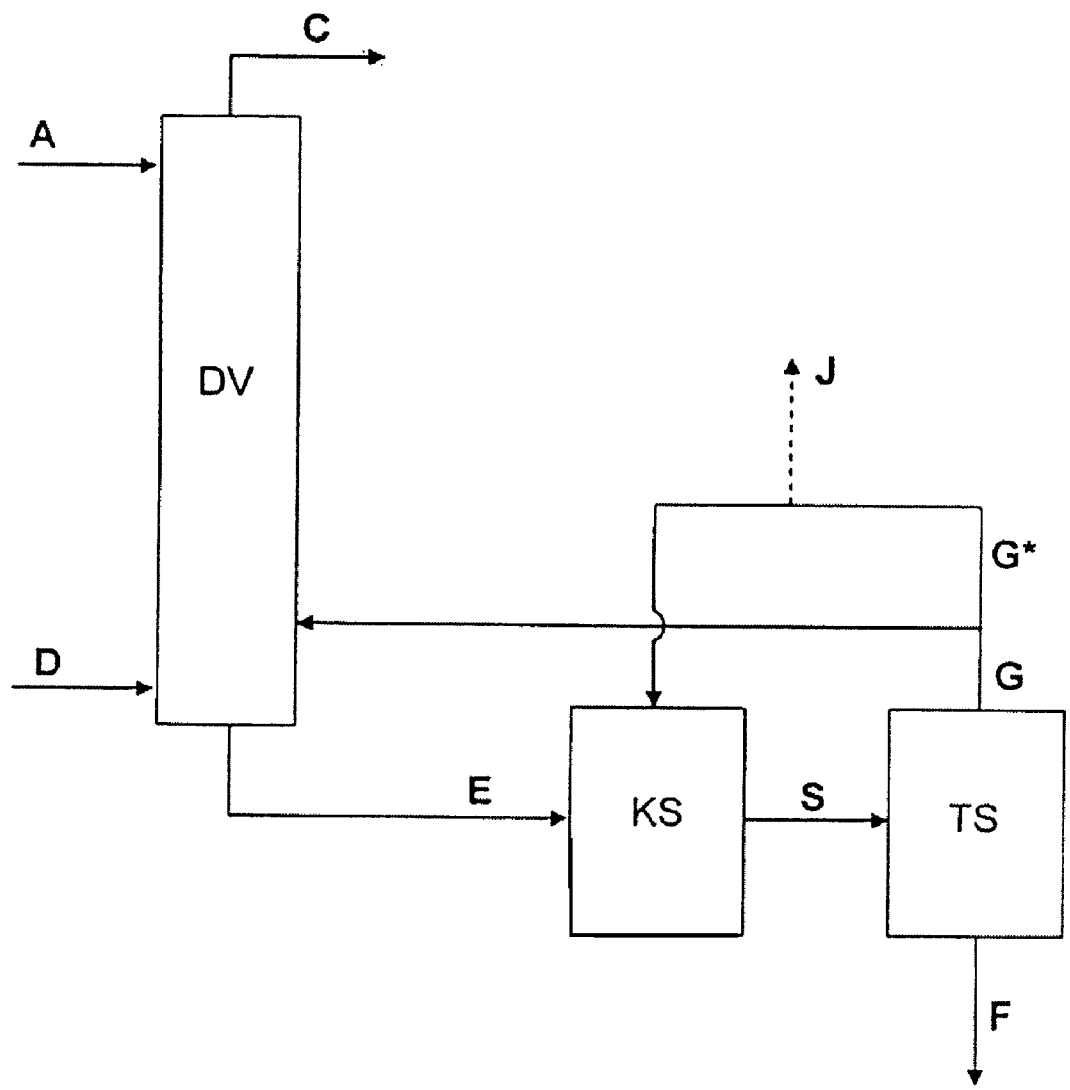

FIG. 3 shows a diagram for carrying out a further variant of the inventive process. In particular, FIG. 3 illustrates preferred embodiments of the inventive process according to the aforementioned steps a) to f) and, g), steps a) to f) and g'), steps aa) to ff) and g), or steps aa) to ff) and g'), respectively.

In detail, in the process shown in FIG. 3, generally a procedure is followed such that a sodium-comprising base (A)-comprising aqueous solution or suspension is fed to the top of the distillation apparatus (DV), in particular of a distillation column (step aa)). The mother liquor (G) is partially fed in the lower region of the distillation apparatus (DV), the sodium-formate- and formic-acid-comprising mixture (B) being obtained (step bb)). The water (C) is ejected at the top of the distillation apparatus (DV) (step cc)). The mixture (B) from step bb) is admixed with the formic acid (D) in the distillation apparatus (DV) to obtain the aqueous solution (E) (step dd)). The aqueous solution (E) obtained from step dd) is taken off at the bottom of the distillation apparatus (DV), fed to a crystallization stage (KS) and admixed in the crystallization stage (KS) with the subquantity (G*) withdrawn from the mother liquor (G) (steps ee) and g) or g'), respectively). Alternatively, as is obvious to the skilled person, admixing of the aqueous solution (E) with the subquantity (G*) may be carried out before introduction of the combined streams (E) and (G*) into the crystallization stage (KS). In the crystallization stage (KS) the aqueous solution (E) is brought to crystallization to obtain the suspension (S) comprising the solid phase (F) and the mother liquor (G) (step ee)). The suspension (S) from step ee) is fed to a separation stage (TS) in which the solid phase (F) is separated off from the mother liquor (G), moist sodium diformate being obtained as solid phase (F) (step ff)). The mother liquor (G) from step ff) is partially fed in the lower region of the distillation apparatus (DV), after a subquantity (G*) has been removed from the mother liquor (G) (step g) or g'), respectively). The withdrawn subquantity (G*), in total or partially, is used in production of the aqueous solution (E). In one embodiment, the withdrawn subquantity (G*) is fully introduced into the crystallization stage (KS) (step g)). In another embodiment, the withdrawn subquantity (G*) is partially introduced into the crystallization stage (KS), the remaining part (J) of the withdrawn subquantity (G*) being purged or used in production of a sodium-comprising base (A) (step g')). Optionally, the solid phase (F) may be dried by conventional means (not shown).

The examples hereinafter serve to illustrate the invention and are not in any way to be taken as limiting. In this connection, a person skilled in the art will understand that, in particular, the flow rates of material streams specified herein correspond decisively to the apparatus dimensions used. When the inventive process is carried out on an industrial scale, values corresponding proportionally must be used.

EXAMPLES 1 TO 4

Reference is made to the accompanying FIG. 1 which shows a diagram of a process variant of the inventive process. In examples 1 to 4 the mother liquor (G) obtained from the separation stage (TS) is in each case completely recirculated to a bubble-cap tray column having 25 trays (distillation apparatus or distillation column (DV)). The bubble-cap tray column was fitted with a 400 ml circulation evaporator with level control. The discharge proceeded from the bottom by a circulation being generated by means of a K-Engineering pump, on the pressure side of which a solenoid valve was actuated, depending on the bottom level.

At the top of the distillation column (DV), a 40% strength by weight aqueous sodium formate solution (sodium-comprising base (A)) was fed at flow rates in the range from about 120 to 130 g/h in the region of the top tray. The mother liquor (G) was fed in the lower region of the distillation column (DV) about at the height of the fifth tray at flow rates in the range from about 210 to 220 g/h, the sodium-formate- and formic-acid-comprising mixture (B) being obtained. The resultant mixture (B) had the compositions specified respectively in table 1 below. From table 1, likewise, there follow the mean bottom temperatures which are established in each case in the region of the circulation evaporator, and also the pressures established in the bubble-cap tray column. Excess water (C) was discharged at the top of the distillation column (DV) in the region above the top tray. The amounts of water (C) discharged in this case were in each case in the range from about 73 to 88 g/h and comprise formic acid fractions in the range from 0.01 to 0.2% by weight. The mixture (B) was taken off at the bottom of the distillation column (DV). The amounts of mixture (B) discharged in this case were in each case in the range from 258 to 276 g/h.

Subsequently, 94% strength by weight aqueous formic acid (D) was fed to the mixture (B), e.g. in an amount in the range of about 10 to 15% by weight, based on the total weight of the mixture (B). The resultant aqueous solution (E) had in each case compositions defined according to the invention; e.g. 53.5% by weight of formic acid, 38.5% by weight of sodium formate and 8.0% by weight of water. The aqueous solution (E) was fed to the crystallization stage (KS) and was brought herein to crystallization, to obtain the suspension (S) comprising the solid phase (F) and the mother liquor (G). The resultant suspension (S) was fed to the separation stage (TS), in which the solid phase (F) was separated off from the mother liquor (G), moist sodium diformate being obtained as solid phase (F). The resultant solid phase (F) comprised in each case residual amounts of water in the range from 0.6 to 0.9% by weight. The solid phase (F) was dried in each case at a product temperature of 35° C. and a pressure of 50 mbar in a drying cabinet for about 2 h. The resultant solid sodium diformate preparation had a water content of at most 0.1% by weight in each case.

TABLE 1

| Ex. No. (sample No.) | Time [h] | Mean T$_{bottom}$ [° C.] | Pressure [mbar] | Feed G [% by weight] | | | Mixture B [% by weight] | | |
|---|---|---|---|---|---|---|---|---|---|
| | | | | FA | H$_2$O | Nafo | FA | H$_2$O | Nafo |
| 1 (1) | 6 | 112.2 | 400 | 56.7 | 12.3 | 31.0 | 48.2 | 5.9 | 45.9 |
| 1 (2) | 8.5 | 111.7 | 400 | 56.7 | 12.3 | 31.0 | 49.4 | 6.0 | 44.6 |
| 2 (1) | 4.5 | 110.9 | 500 | 56.7 | 12.3 | 31.0 | 46.6 | 9.5 | 43.8 |
| 2 (2) | 6.5 | 110.9 | 500 | 56.7 | 12.3 | 31.0 | 46.9 | 9.6 | 43.6 |
| 2 (3) | 9 | 111.0 | 500 | 56.7 | 12.3 | 31.0 | 46.8 | 9.6 | 43.7 |
| 3 (1) | 5 | 117.3 | 600 | 56.0 | 12.0 | 32.0 | 46.3 | 8.8 | 44.9 |
| 3 (2) | 7.5 | 116.9 | 600 | 56.0 | 12.0 | 32.0 | 47.3 | 9.1 | 43.6 |
| 4 (1) | 6 | 128.1 | 800 | 56.0 | 12.0 | 32.0 | 47.1 | 7.1 | 45.8 |
| 4 (2) | 8 | 126.2 | 800 | 56.0 | 12.0 | 32.0 | 47.4 | 7.0 | 45.7 |

In table 1, FA is formic acid and Nafo is sodium formate. The mean bottom temperature T$_{bottom}$ was measured in the region of the circulation evaporator.

The invention claimed is:

1. A process for producing a solid sodium diformate preparation having a formic acid content of at least 35% by weight based on the total weight of sodium diformate preparation, in which, at elevated temperature, an aqueous solution (E) is produced which comprises sodium formate and formic acid in a molar ratio of HCOOH:HCOONa of greater than 1.5:1 and which has a molar ratio of HCOOH:H$_2$O of at least 1.1:1, the aqueous solution (E) is brought to crystallization to obtain a solid phase (F) and a mother liquor (G), and the solid phase (F) is separated off from the mother liquor (G), (i) the mother liquor (G), in total or partially, being fed to a distillation apparatus (DV);

(ii) the mother liquor (G) in the distillation apparatus (DV) being admixed with a sodium-comprising base (A) to obtain a mixture (B) comprising sodium formate and formic acid;

(iii) admixing the mixture (B) obtained from step (ii) with formic acid (D) to obtain the aqueous solution (E); and (iv) excess water (C) essentially being ejected only by withdrawal from the distillation apparatus (DV).

2. The process according to claim 1, wherein, in step (i), the mother liquor (G) is fed partially to the distillation apparatus (DV) after a subquantity (G*) has been removed from the mother liquor (G).

3. The process according to claim 2, wherein the withdrawn subquantity (G*), in total or partially, is used in production of the aqueous solution (E).

4. The process according to claim 2, wherein the amount of the withdrawn subquantity (G*) is less than 30% by weight, based on the total weight of the mother liquor (G).

5. The process according to claim 1, wherein, in step (i), the mother liquor (G) is fed in the lower region of the distillation apparatus (DV).

6. The process according to claim 1, wherein, in step (ii), the sodium-comprising base (A) is fed at the top of the distillation apparatus (DV).

7. The process according to claim 1, wherein, in step (iv), the water (C) is ejected at the top of the distillation apparatus (DV).

8. The process according to claim 1, wherein, in step (iii), the mixture (B) obtained from step (ii) is taken off from the distillation apparatus (DV), admixed with the formic acid (D) to obtain the aqueous solution (E), and the resultant aqueous solution (E) is fed to a crystallization stage (KS).

9. The process according to claim 1, wherein, in step (iii), the formic acid (D) is fed in the lower region of the distillation apparatus (DV) comprising the mixture (B) and the aqueous solution (E) obtained in this manner at the bottom of the distillation apparatus (DV) is fed to a crystallization stage (KS).

10. The process according to claim 9, wherein the formic acid (D) is fed below the feed of the sodium-comprising base (A) and below the feed of the mother liquor (G).

11. The process according to claim 1, wherein, in step (iii), the mixture (B) obtained from step (ii) is taken off from the distillation apparatus (DV), fed to a crystallization stage (KS) and, in the crystallization stage (KS), admixed with the formic acid (D) to obtain the aqueous solution (E).

12. The process according to claim 1, wherein the aqueous solution (E) or the mixture (B) is taken off at the bottom of the distillation apparatus (DV).

13. The process according to claim 1, wherein a suspension (S) obtained downstream of the crystallization stage (KS) is fed to a separation stage (TS) to separate off the solid phase (F) from the mother liquor (G).

14. The process according to claim 1, wherein the distillation apparatus (DV) is a distillation column selected from tray columns, columns having fixed internals, random-packing columns, and ordered-packing columns.

15. The process according to claim 14, wherein the distillation column is a tray column having a number of trays in the range from 10 to 40.

16. The process according to claim 14, wherein a reflux ratio in the distillation apparatus (DV) is in the range from 0 to 5.

17. The process according to claim 1, wherein the pressure in the distillation apparatus (DV) is in the range from 100 to 1500 mbar.

18. The process according to claim 1, wherein the temperature in the distillation apparatus (DV) is in the range from 60 to 200° C.

19. The process according to claim 1, wherein the sodium-comprising base (A) is selected from sodium formate, sodium hydroxide, sodium carbonate, sodium hydrogencarbonate, sodium $C_1$-$C_6$-alkanoates and mixtures thereof.

20. The process according to claim 1, wherein, in step (ii), the sodium-comprising base (A) is fed to the distillation apparatus (DV) in the form of an aqueous solution or suspension.

21. The process according to claim 20, wherein the sodium-comprising base (A)-comprising aqueous solution or suspension has a water content in the range from 10 to 80% by weight, based on the total weight of the aqueous solution or suspension.

22. The process according to claim 20, wherein, as sodium-comprising base (A), use is made of sodium formate in the form of an aqueous solution or suspension which comprises sodium formate in an amount in the range from 20 to 90% by weight, based on the total weight of the sodium formate solution or suspension.

23. The process according to claim 20, wherein, as sodium-comprising base (A), use is made of NaOH in the form of an aqueous sodium hydroxide solution which has an NaOH content in the range from 20 to 90% by weight, based on the total weight of the aqueous sodium hydroxide solution.

24. The process according to claims 20, wherein, in step (ii), the mother liquor (G) is admixed with an amount of the sodium-comprising base (A)-comprising aqueous solution or suspension such that the resultant mixture (B) has a water content of at most 20% by weight, based on the total weight of the mixture (B).

25. The process according to claim 1, wherein, in step (ii), the mother liquor (G) is admixed with an amount of the sodium-comprising base (A) such that the molar ratio of HCOOH:HCOONa in the resultant mixture (B) is in the range from 1:1 to 2:1.

26. The process according to claim 20, wherein, in steps (i) and (ii), the weight ratio of the sodium-comprising base (A)-comprising aqueous solution or suspension to the mother liquor (G) which is fed in each case to the distillation apparatus (DV) is in the range from 2:1 to 1:6.

27. The process according to claim 1, wherein, in step (iii), at least 80% strength by weight aqueous formic acid (D) is fed.

28. The process according to claim 1, wherein the formic acid (D) fed in step (iii) has a water content such that the resultant aqueous solution (E) has a water content of at most 25% by weight, based on the total weight of the aqueous solution (E).

29. The process according to claim 1, wherein the solid sodium diformate preparation has a formic acid content in the range from 38 to 41% by weight, based on the total weight of the sodium diformate preparation.

30. The process according to claim 1, wherein the solid sodium diformate preparation, if appropriate after a drying step, has a water content of no greater than 0.5% by weight, based on the total weight of the preparation.

\* \* \* \* \*